United States Patent [19]
Bobb et al.

[11] Patent Number: 5,047,626
[45] Date of Patent: Sep. 10, 1991

[54] OPTICAL FIBER SENSOR FOR MEASURING PHYSICAL PROPERTIES OF LIQUIDS

[75] Inventors: Lloyd C. Bobb, Warminster; Barbara J. White, Hatboro; Jon P. Davis, Willow Grove, all of Pa.

[73] Assignee: The United States of America as represented by the Secretary of the Navy, Washington, D.C.

[21] Appl. No.: 460,435

[22] Filed: Jan. 3, 1990

[51] Int. Cl.$^5$ .............................................. H01J 5/16
[52] U.S. Cl. ............................ 250/227.19; 250/231.10
[58] Field of Search ....................... 250/227.19, 231.1; 324/96; 350/96.29; 356/44, 72, 357-359

[56] References Cited

U.S. PATENT DOCUMENTS

| | | | |
|---|---|---|---|
| 4,530,603 | 7/1985 | Shaw et al. | 250/227.19 |
| 4,563,639 | 1/1986 | Langeac | 250/227.17 |
| 4,621,929 | 11/1986 | Phillips | 356/44 |
| 4,627,728 | 12/1986 | Willson | 250/227.19 |
| 4,929,050 | 5/1990 | Wilson | 250/227.19 |

*Primary Examiner*—David C. Nelms
*Assistant Examiner*—Stephone Allen
*Attorney, Agent, or Firm*—James V. Tura; James B. Bechtel; Susan E. Verona

[57] ABSTRACT

A physical property of a liquid or of any optical fiber is measured using an optical fiber interferometer. A conductive material is disposed upon the surface of a region of a light transmitting optical fiber and the region having the conductive material is disposed in the liquid. Light energy is applied to one end of the fiber and transmitted light is received at the other end of the fiber. Electrical energy is applied to the conductive material disposed upon the surface of the fiber to heat the region of the fiber and cause a change in the optical path length of the light transmitted through the fiber. The physical property of the liquid or optical fiber is determined in accordance with the change in the optical path length of the received light caused by applying the electrical energy to the conductive material. A series of short energy pulses is provided and the average phase change is determined. The conductive material is gold and it encircles the fiber. The gold may be disposed on the jacket of the fiber or the jacket may be removed before disposing the gold.

16 Claims, 3 Drawing Sheets

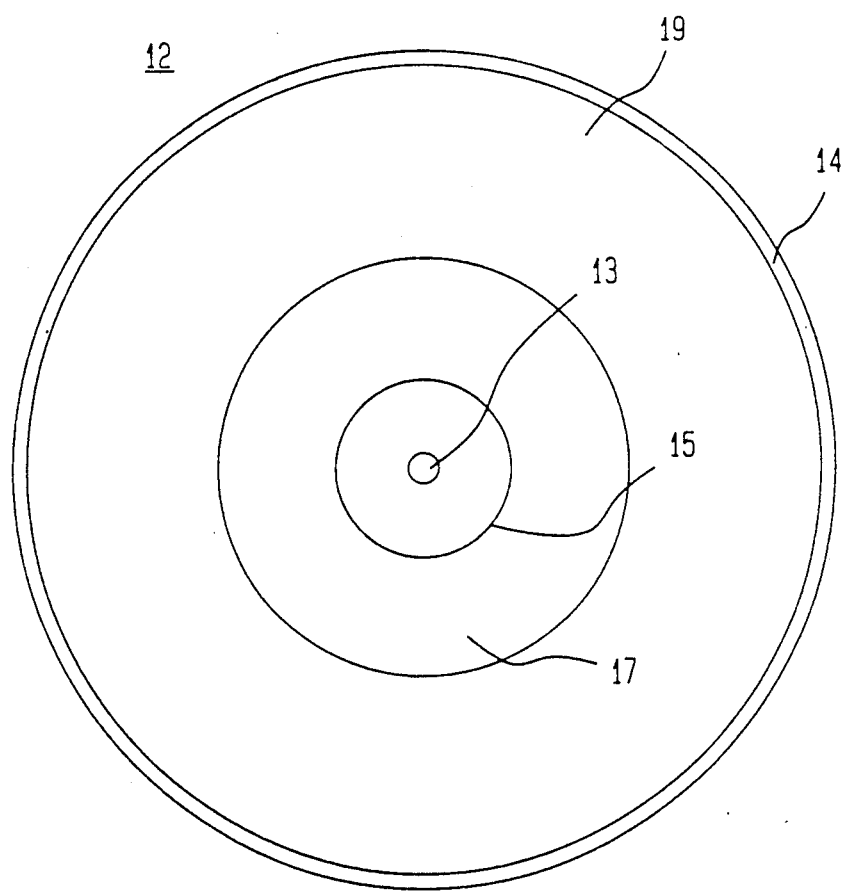

1

OPTICAL FIBER SENSOR FOR MEASURING PHYSICAL PROPERTIES OF LIQUIDS

STATEMENT OF GOVERNMENT INTEREST

The invention described herein may be used by and for the Government of the United States of America for governmental purposes without the payment of any royalties thereon or therefor.

BACKGROUND OF THE INVENTION

This invention relates to a device for measuring the physical properties of liquids and in particular to a device for measuring physical properties of liquids using the interference of light waves.

It is well known in the art to use fiber optic systems for temperature measurement and monitoring of liquids. For example, these systems are commonly used when monitoring the temperature of flammable liquids because non-electrical sensing devices eliminate a source of explosion hazard associated with electrical temperature monitoring systems.

The thermal conductivities of liquids are often measured because the thermal conductivities of liquids are required for various heat transfer analyses. These conductivities are commonly obtained with a transient hot-wire apparatus. In this technique a thin platinum wire, serving as both a heating element and a thermometer, is heated resistively with a current pulse of about one second duration. The thermal conductivity of the surrounding medium is determined from the temperature change of the wire as a function of time. In this type of analysis an approximate solution of the heat conduction equation is used, where the slope of the change in temperature versus the natural log of time curve is inversely proportional to the thermal conductivity of the medium. In applying this method, a number of corrections are necessary due to the finite diameter and finite thermal conductivity of the platinum wire. Additionally, a correction for the temperature dependence of the fluid properties is necessary. With these corrections incorporated into the analysis, the technique allows for thermal conductivity determinations with an accuracy of 0.2%.

Another method for measuring temperature using an optical fiber is disclosed in Langeac U.S. Pat. No. 4,563,639. In the apparatus of Langeac, a probe is formed by winding an optical fiber in a generally solenoid shape. U.S. Pat. No. 4,621,929, issued to Phillips and entitled "Fibre Optic Thermal Anemometer," teaches a device for measuring the heat transfer coefficient of a sample.

SUMMARY OF THE INVENTION

A physical property of a liquid is measured using a light transmitting optical fiber interferometer. A conductive material is disposed upon the surface of a region of the light transmitting optical fiber and the region having the conductive material is disposed in the liquid. Light energy is applied to one end of the fiber and transmitted light is received at the other end of the fiber. Electrical energy is applied to the conductive material disposed upon the surface of the fiber to heat the region of the fiber and cause a change in the optical path length of the light transmitted through the fiber. The physical property of the liquid or optical fiber is determined in accordance with the change in the interference pattern of the received light.

BRIEF DESCRIPTION OF THE DRAWINGS

FIGS. 2a and 2b show cross-sectional representations of a conductor coated region of an unjacketed optical fiber and a jacketed optical fiber, respectively, of the thermal conductivity cell of the present invention.

DETAILED DESCRIPTION OF THE INVENTION

Figure 2A:
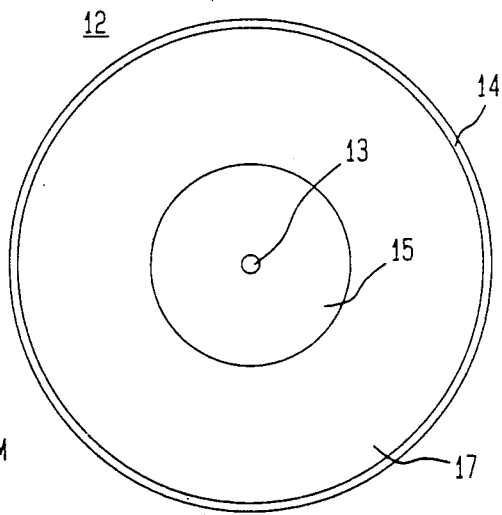
Figure 1:
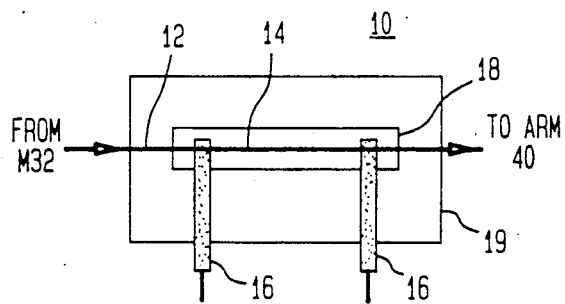
FIG. 1 shows the thermal conductivity cell of the optical fiber sensor of the present invention for measuring thermal conductivity.

Referring now to FIGS. 1, 2a,b, there is shown thermal conductivity cell 10 and a cross-sectional view of optical fiber 12 of thermal conductivity cell 10 for measuring physical properties of a liquid. In thermal conductivity cell 10 there is provided a thin layer 14 formed of gold and disposed on the surface of optical fiber 12 either on the outer surface of silica substrate 17 or on the outer surface of jacket 19 surrounding silica substrate 17. Gold layer 14 may be sputtered onto the surface of fiber 12 and may have a thickness of approximately one-tenth of a micron. The section of fiber 12 having gold layer 14 is disposed in well 18 of block 19. The liquid being monitored is placed in well 18 to permit immersion of gold layer 14 in the liquid.

Electrical energy is applied to gold layer 14 and the temperature rise of optical fiber 12 due to the applied electrical energy is determined by measuring the change in optical path length in optical fiber 12. This temperature is influenced by the thermal conductivity of the liquid. Thus, the thermal conductivity of the liquid may be determined in accordance with the measured light. This thermal conductivity measurement requires a temperature rise of only tenths of degree of the optical fiber in thermal conductivity cell 10; the corrections associated with the temperature dependence of the fluid properties are unnecessary.

In addition, heat conduction is determined numerically for the regions inside and outside of fiber 12 so that no corrections associated with the approximate solution are required. Another advantage associated with the short-time measurement of the thermal conductivity cell 10 is the minimization of possible convective losses which would unnecessarily complicate the thermal conductivity determination. The time delay associated with the onset of convection is much greater than the pulse times used.

Single-mode optical fiber 12 of thermal conductivity cell 10 of the present invention may be an ITT Type T-1601 having a four micron diameter silica core 13, a forty micron outside diameter $B_2O_3$-doped silica cladding 15, an eighty-five micron outside diameter silica substrate 17, and a silicone/plastic jacket 19. Jacket 19 may be removed from a section of fiber 12 over a length of fiber 12 which may be approximately two and one-half centimeters. Gold film 14 is sputtered onto the surface of fiber 12 completely encircling the region wherein jacket 19 is removed. Alternately, gold film 14 may be deposited directly on jacket 19.

Figure 3:
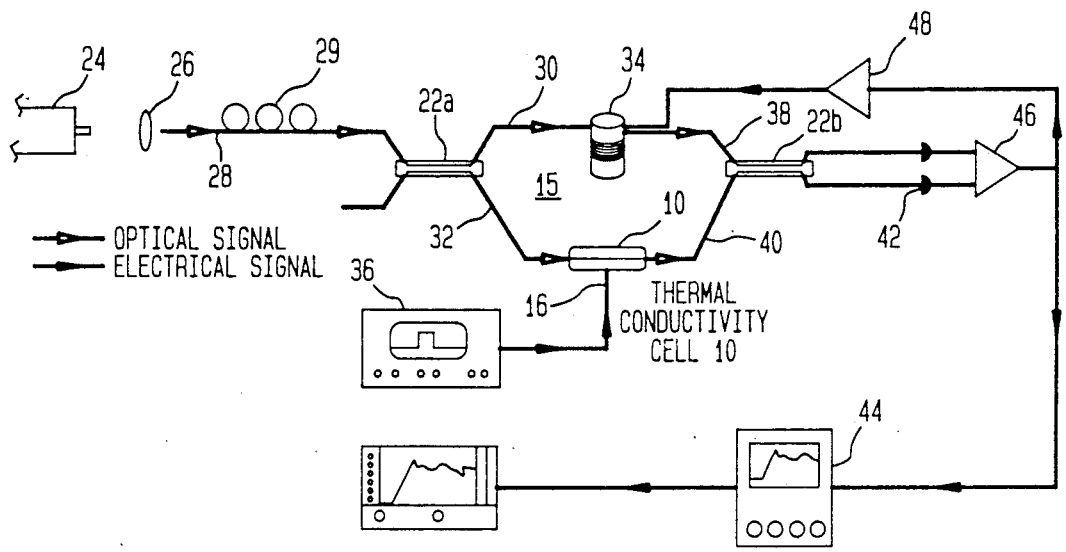
FIG. 3 shows the experimental apparatus used to test the thermal conductivity sensor of the present invention including a Mach-Zehnder interferometer.

Referring now to FIG. 3, there is shown Mach-Zehnder interferometer system 20 wherein thermal conductivity cell 10 forms one arm of Mach-Zehnder interferometer 15. Interferometer system 20 also includes single-mode couplers 22a,b which may be 3dB 2×2 Amphenol couplers. Light from single-frequency heliumneon laser 24 is applied by way of lens 26 to the end of input fiber 28 having polarization controller 29. The light is split evenly between arms 30, 32 of interferometer 15 at first coupler 22a. Arm 30 of interferometer 15 includes a PZT stretcher 34 to maintain interferometer 15 at quadrature. Arm 32 of interferometer 15 is coupled to thermal conductivity cell 10. Electrodes 16 are electrically coupled to gold layer 14 of fiber 12 with silver paint. Gold layer 14 is then immersed in the fluid medium whose thermal conductivity is to be determined. Approximately 1.4 cubic centimeters of the fluid are sufficient for this measurement. The light from arms 38, 40 is combined at coupler 22b and exits through coupler 22b and is collected by photodiodes 42 for comparison by differential amplifier 46. Feedback from differential amplifier 46 is applied to PZT fiber stretcher 34 by way of locking amplifier 48.

Gold-coated fiber 12 is resistively heated repeatedly with one millisecond voltage or current pulses with a one percent duty cycle from pulse generator 36. Thus the single section of fiber 12 having gold layer 14 disposed thereupon serves as both the heating element and the thermometer of interferometer system 20. The pulses from pulse generator 36 are applied to gold-coated fiber 12 by way of electrodes 16. Each pulse from pulse generator 36 produces a time-dependent signal which is proportional to the optical phase change in arm 32 containing thermal conductivity cell 10 because temperature changes of fiber 12 within gold layer 14 are observed as a shifting of the interference pattern. These signals are recorded and stored by signal analyzer 44. Signal analyzer 44 may, for example, be an HP 3651A Signal Analyzer. The time-averaged signal produced by one hundred such pulses was recorded.

The temperature sensitivity of gold-coated fiber 12 may be determined both theoretically and experimentally. In the experimental determination, microdegree temperature changes are observed. In the theoretical determination, the phase of a wave propagating in fiber 12 of length L is given by $$\phi = 2\pi nL/\lambda \quad (1)$$

where n is the effective refractive index, which may be approximated by the refractive index of the core of fiber 12, and $\lambda$ is the wavelength of the light in free space. A change in fiber 12 temperature $\Delta T$ results in a phase shift $\Delta\phi$ of the light in fiber 12 because of the temperature-induced change in the refractive index of the core of fiber 12, the change in the length of fiber 12 due to thermal expansion, and the photoelastic effect. The temperature sensitivity of the gold-coated section 14 fiber 12 may be expressed as $$\Delta\phi/(L\Delta T) = (2\pi/\lambda)[(\rho n/\rho T) - n\epsilon_z/\Delta T - (n^3/2\Delta T)[(P_{11}+P_{12})\epsilon_r - P_{12}\theta_z]] \quad (2)$$

where $\rho$ is the core density, $\epsilon_z$ and $\epsilon_r$ are the axial and radial strains, and $P_{11}$ and $P_{12}$ are the Pockels coefficients. Fiber 12 is considered to consist of four concentric layers: the core, the cladding, the substrate, and the one-tenth micron gold layer 14. The strains resulting from the temperature change $\Delta T$ are calculated using the method of Schuetz et al. The sensitivity for the unjacketed fiber thus determined is $\Delta\phi/L\Delta T = 16.3$ fringes/m-° C. where the first term in Eq. (2) provides the major contribution.

The temperature sensitivity of gold-coated fiber 12 may also be determined experimentally by monitoring the resistance change of the gold film 14 when heated by a steady current. The temperature change is then calculated as $$\Delta T = \Delta R/Ry_t \quad (3)$$

Where $\Delta R$ is the resistance change corresponding to a temperature change $\Delta T$, R is the room temperature resistance, and $y_t$ is the temperature coefficient of resistivity. A value for $y_t$ is determined experimentally by placing gold layer 14 of fiber 12 in a furnace (not shown) and monitoring the resistance as the temperature is increased. These experimental results are then used to obtain the experimental temperature sensitivity of $$\Delta\phi/L\Delta T = 15.9 \text{ fringes/m-}° C. \quad (4)$$

The experimental value is in reasonable agreement with the theoretical value, and is the value used in the thermal conductivity analyses. The greatest experimental uncertainty is the accurate determination of the coated length L of fiber 12. In practice it is most convenient to calibrate the thermal conductivity sensor with a fluid of known thermal conductivity; in the measurements discussed below, pure ethylene glycol is taken as a standard with a thermal conductivity of 0.255W/m-° C.

Figure 4:
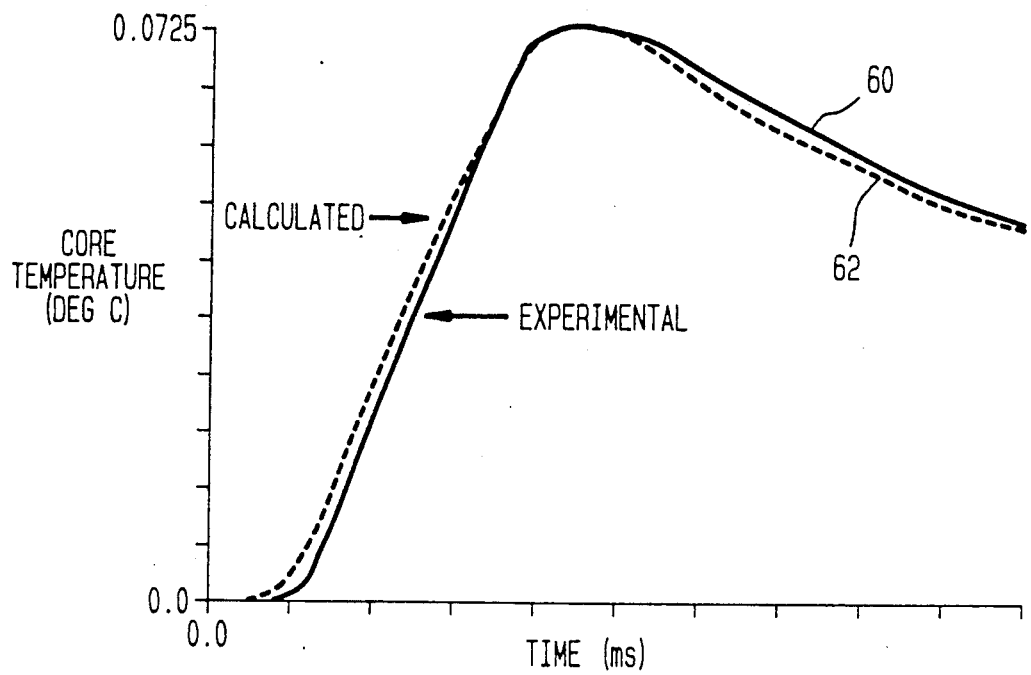
FIG. 4 shows the core temperature of the fiber of FIG. 1 as a function of time when a one millisecond square pulse is applied to a conducting region disposed on the surface of the fiber of FIG. 1.

The experimental data are recorded as optical phase changes $\Delta\phi$ which are related to $\Delta T$ through equation 4. A typical plot of $\Delta T$ versus time t for water is shown as curves 60,62 in FIG. 4, wherein curve 60 represents the experimentally obtained response and curve 62 represents the calculated response. Curve 60 represents the average response to one hundred consecutive one millisecond pulses. If gold-coated fiber 12 is immersed in a fluid medium of lower thermal conductivity, the risetime of curve 60 is shorter, the peak is higher and the decay time is longer. The peak value of the temperature rise provides the most convenient measure of the thermal conductivity; thus, the data presented below are obtained through measurement of the peak heights.

An interpretation of the experimental data is provided through a numerical solution of the heat conduction equation.

$$\iota\Delta T/\iota t = k\nabla^2\Delta T - P/\rho C_p A \quad (5)$$

Where $k = K/\rho C_p$ is the diffusivity, K is the thermal conductivity, $C_p$ is the specific heat at constant pressure. A is the cross-sectional area of the heated region, P is the power applied to the fiber per unit length, and $\rho$ is the density. An infinite length and circular symmetry are assumed, and equation (5) is solved in two regions: the silica fiber and the surrounding liquid medium whose thermal conductivity is to be determined. The material properties $\rho$ and $C_p$ for both the fiber 12 and the medium must be separately measured, obtained from the literature, or determined by the present method. Equation (5) is replaced by a finite difference equation which is solved using boundary conditions $\iota\Delta T/\iota r = 0$ at $r=0$ and $\Delta T=0$ at $r=R$ and initial conditions $\Delta T=0$. The outer radius R of the medium is taken to be much greater than the thermal diffusion length for the time period employed in the calculation. Gold coating 14 is assumed to have a negligible thickness and the power dissipation in gold coating 14 is assumed to occur in the boundary region between the fiber 12 and the fluid medium. The finite-difference approximations yield a set of coupled first-order ordinary differential equations in the time variable. These differential equations are then solved by the standard Bulirsch-Stoer Method.

The entire $\Delta T$ versus time curve is a sensitive function of the material parameters. For example, a five micron change in the fiber outer-diameter used in the calculations produces an easily discernible change in the calculated curve 62. Thus the method of the present invention may be used to determine the parameters of fiber 12 as well as the properties of the liquid. The calculations for curve 62 are performed using a handbook value of $K_{silica} = 1.34$ W/m-°C, a value for generic silica. A ten percent reduction of $K_{silica}$ to 1.21 W/m-°C makes the calculated and experimental curves almost indistinguishable at the resolution shown in FIG. 4.

Experimental results are presented for aqueous ethylene glycol solutions. Handbook values of the density and specific heat and literature values of the thermal conductivity are shown in Table 1.

TABLE 1

| Concentration (Weight % eth.gly) | Solution Properties at 20° C. | | |
|---|---|---|---|
| | Density (kg/m³ × 10⁻³) | Specific Heat (J/kg °C. × 10⁻³) | Thermal Conductivity (W/m-°C.) |
| 0 | 1.000 | 4.186 | 0.599 |
| 20 | 1.0241 | 3.906 | 0.508 |
| 40 | 1.0514 | 3.516 | 0.423 |
| 60 | 1.0765 | 3.119 | 0.356 |
| 80 | 1.0960 | 2.729 | 0.298 |
| 100 | 1.1130 | 2.344 | 0.255 |

Figure 5:
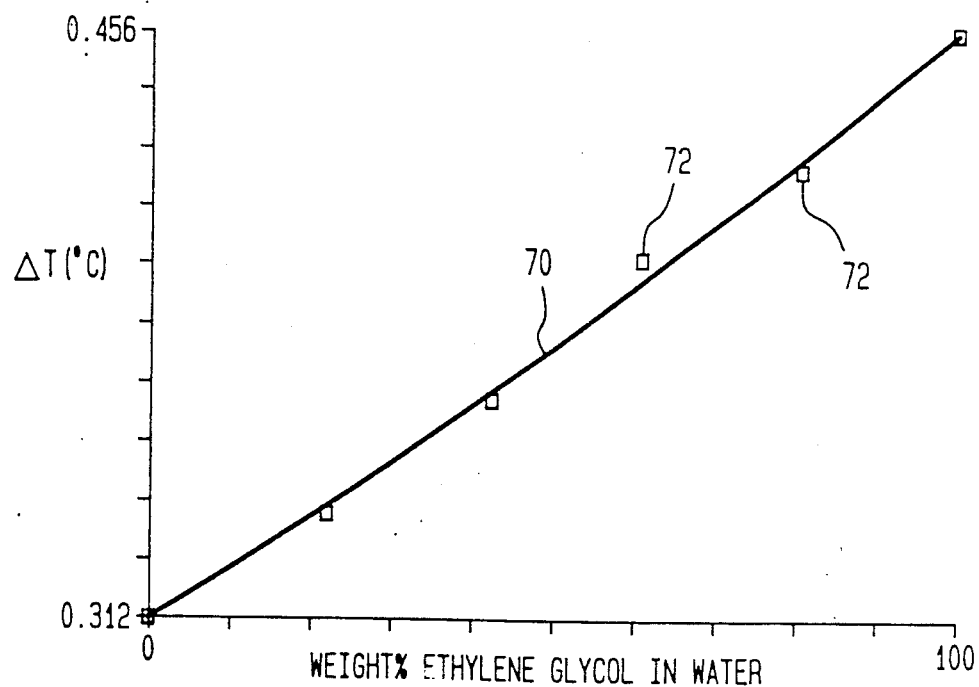
FIG. 5 shows a graphical representation of the variation of peak core temperature of the fiber of FIG. 1 as a function of the concentration of ethylene glycol plus water mixtures.

The data given in Table 1 are used to calculate the maximum core temperatures for an applied power of 5.90 W/m for the six solutions. The maximum core temperatures are also measured for solutions of 0, 20, 40, 60, 80, and 100% ethylene glycol by volume. The experimental and calculated results are shown as points 72 and curve 70 respectively in FIG. 5. Similar agreement is obtained for other power levels. Conversely, thermal conductivity cell 10 of the present invention may be used to measure the concentration as well as the diffusivity and other physical properties of a liquid.

Thermal conductivities may also be determined for several ethylene glycol solutions using an optical fiber thermal conductivity sensor such as thermal conductivity cell 10. A short-time technique may be used wherein solution temperature changes of tenths of a degree are produced. The classical hotwire approach uses heating times of longer duration and produces larger temperature changes in the fluid being measured. For this reason many corrections are required for accurate measurements. The short-time approach eliminates these corrections but requires a more complex numerical solution of heat conduction equation 5.

The heat capacity of gold layer 14 itself has been ignored. This effect is most important at early times and produces a temperature reduction of less than two percent for times greater than one tenth of a millisecond. The second effect ignored is the temperature non-uniformity of fiber 12. This effect is also most important at early times and appears as a temperature increase of less than one percent of peak value for the first couple tenths of a millisecond.

For well-known fiber material parameters the present technique can determine $(PC_p)$ as well as K for the medium. Equation (5) is invariant on multiplication of $\Delta T$ and $(P/PC_pA)$ by the same factor. Therefore, normalized plots of $\Delta T$ versus time will depend only on $k_{medium}$ ($k_{medium} = K/PC_p$) = diffusivity. $k_{medium}$ can thus be obtained from the normalized plots. Knowing $k_{medium}$, P, and A, the peak height gives $(PC_p)$ which can then be used to obtain $K_{medium}$.

A gold-coated jacketed fiber 12 or a gold-coated unjacketed fiber 12 may be provided for conductivity cell 10 of the present invention. Thermal conductivity cell 10 formed with a gold-coated jacketed fiber 12 is more than twice as sensitive as gold-coated unjacketed fiber 12.

Those skilled in the art will appreciate without any further explanation that many modifications and variations are possible to the above disclosed optical fiber sensor for measuring thermal conductivity embodiments, within the concept of this invention. Consequently, it should be understood that all such modifications and variations fall within the scope of the following claims.

What we claim is:

1. A method for measuring a physical property of a liquid using a light transmitting optical fiber having an optical path length, comprising the steps of:
   (a) disposing a conductive material upon the surface of a region of said light transmitting optical fiber;
   (b) disposing at least a portion of said fiber region having said conductive material in said liquid;
   (c) applying light energy to a first end of said light transmitting optical fiber;
   (d) thermally changing said optical path length in response to electrical energy applied to said conductive material while said fiber is disposed in said liquid;
   (e) receiving transmitted light at a second end of a said optical fiber,
   (f) determining the change in said optical path length in accordance with said received light; and,
   (g) determining said physical property of said liquid in accordance with said thermally changed optical path length.

2. The method of claim 1, wherein step (f) comprises determining said change in said optical path length in accordance with the change inn phase of said received light when said electrical energy is applied to said conductive material.

3. The method of claim 1, wherein step (d) comprises the step of applying a substantially short electrical energy pulse.

4. The method of claim 3, wherein step (d) comprises applying an electrical energy pulse of approximately one millisecond duration.

5. The method of claim 1, comprising the further step of applying a plurality of electrical energy pulses.

6. The method of claim 5, wherein data representative of received light for a plurality of electrical energy pulses are averaged.

7. The method of claim 1, wherein step (d) comprises raising the temperature of said region a few tenths of a degree.

8. The method of claim 1, wherein step (a) comprises the step of disposing said conductive material upon a jacket of said optical fiber.

9. The method of claim 1, wherein step (a) is preceded by the step of removing a fiber jacket from said optical fiber.

10. The method of claim 1, wherein step (a) comprises encircling said optical fiber with said conductive material.

11. The method of claim 10, wherein step (a) comprises encircling said optical fiber with a layer of conductive material having a thickness of approximately one-tenth micron.

12. The method of claim 1, wherein step (a) comprises disposing said conductive material upon the surface of a region of said optical fiber wherein the region has a length of approximately one inch.

13. The method of claim 1 wherein step (a) comprises disposing gold upon the surface of said optical fiber.

14. The method of claim 1, wherein step (g) comprises determining the thermal conductivity of said liquid in accordance with said received light.

15. The method of claim 1, wherein step (f) comprises determining the diffusivity of said liquid in accordance with said received light.

16. The method of claim 1, wherein step (f) comprises determining a parameter of said optical fiber in accordance with said received light.

* * * * *